United States Patent

Czech

[11] Patent Number: 5,064,955
[45] Date of Patent: Nov. 12, 1991

[54] LARGE SCALE, NON-CHROMATOGRAPHIC PURIFICATION OF CHROMOGENIC CRYPTAHEMISPHERANDS (1.1) AND (2.1)

[75] Inventor: Bronislaw P. Czech, Peekskill, N.Y.

[73] Assignee: Technicon Instruments Corporation, Tarrytown, N.Y.

[21] Appl. No.: 533,058

[22] Filed: Jun. 4, 1990

[51] Int. Cl.$^5$ .......................................... C07D 273/08
[52] U.S. Cl. ................................................... 540/469
[58] Field of Search ........................................ 540/469

[56] References Cited
U.S. PATENT DOCUMENTS
4,845,212  7/1989  Czech .................................. 540/469

*Primary Examiner*—Nicholas S. Rizzo
*Attorney, Agent, or Firm*—Jeffrey M. Greenman

[57] ABSTRACT

A process is disclosed for the non-chromatographic purification of chromogenic cryptahemispherands of the following general formula (II) which are capable of selective binding of sodium ion in aqueous solution:

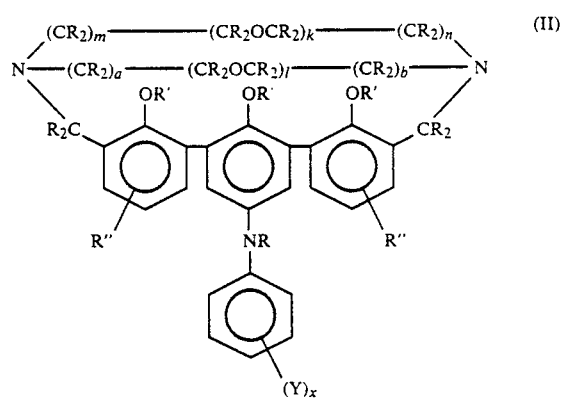

wherein:
R, same or different, is hydrogen, lower alkyl, lower alkylidene, lower alkenyl, allyl, aryl or benzyl;
R', same or different, is lower alkyl, lower alkylidene, lower alkenyl, allyl, aryl or benzyl;
R", same or different, is hydrogen, lower alkyl, lower alkylidene, lower alkenyl, allyl, aryl or benzyl;
Z is halogen;
Y is electron withdrawing group, e.g. CN, NO$_2$, CF$_3$, COOR;
m is 1 to 3;
n is 1 to 3;
a is 1 to 3;
b is 1 to 3;
k is 1 to 2;
l is 1 to 2;
k and l are not both 2; and
x is 2 to 4.

The compound of formula (II) is isolated from the reaction mixture by consecutive treatment of the crude reaction product with suitable solents in order to separate unreacted organic components, inorganic material, and polymers and provide a sodium-free final product.

8 Claims, No Drawings

LARGE SCALE, NON-CHROMATOGRAPHIC PURIFICATION OF CHROMOGENIC CRYPTAHEMISPHERANDS (1.1) AND (2.1)

BACKGROUND OF THE INVENTION

1. Field of the Invention

The present invention relates to a large scale, non-chromatographic purification of chromogenic cryptahemispherands or lithium cryptahemispheraplexes which incorporate diaza-12-crown-4, diaza-14-crown-4 and diaza-15-crown-5 subunits and which are highly selective in binding of sodium ion in aqueous media.

2. Description of the Prior Art

In two review articles, Takagi, et al., "Crown Compounds as Alkali and Alkaline Earth Metal Ion Selective Chromogenic Reagents" Top. Curr. Chem. 121, 1984, pp. 39-65, and Lohr, et al., "Chromoand Fluoroionophores. A New Class of Dye Reagents" Acc. Chem. Res. 18, 1985, pp. 65-72, describe a great variety of chromogenic compounds based on macrocyclic polyethers (corands) which selectively bind metal ions producing a spectral shift in the chromophore. In most reported cases, chromatographic separation was the preferred means of purification of final chromgenic compounds. Much less frequently, when the chromogenic compound happened to be crystalline, recrystallization was used to obtain the pure product. Although chromatography is a powerful separation tool, its use becomes problematic in cases where chromogenic compounds bind ions very strongly. This issue is especially critical when purifying chromogenic compounds which show extremely high propensity toward sodium ion. Sodium ions are abundantly present in commonly used chromatographic materials such as silica gel and alumina, and can easily be scavenged by the chromoionophore during its attempted purification. It should be pointed out that such a danger of "poisoning" by complexed ionic species does not exist in case of chromogenic compounds derived from corands which are relatively weak binders. Additionally, the chromatographic purification is cumbersome and not cost-effective for large scale manufacture.

To date, only a few chromoionophores derived from much stronger macrocyclic binders such as spherands, hemispherands and cryptahemispherands have been reported. Cram, et al., "Host-Guest Complexation. 45. Highly Preorganized Chromogenic Spherands Indicator System Specific for Sodium and Lithium Ions" J. Am. Chem. Soc. 110, 1988, pp. 574, describe a chromogenic spherand of the general formula (I) below, which, due to its powerful binding, extracts sodium ions from Pyrex ® and Kymax ® volumetric flasks.

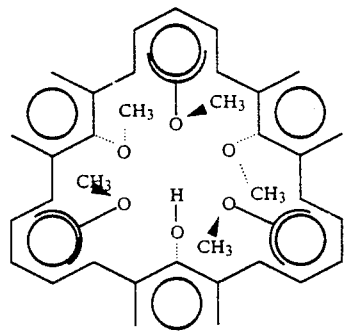

(I)

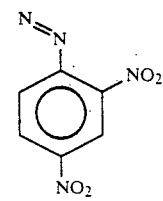

Chromogenic cryptahemispherands and their synthesis are described by Helgeson, et al., "Host-Guest Complexation. 50. Potassium and Sodium Ion-Selective Chromogenic Ionophores" J. Am. Chem. Soc. 111, 1989, pp. 6639-6650, and in U.S. Pat. No. 4,859,606 on which I am named as a co-patentee. These chromogenic cryptahemispherands are used in colorimetric assays of sodium and potassium in blood and other biological fluids. Such compounds can be presented as the following general formula (II)

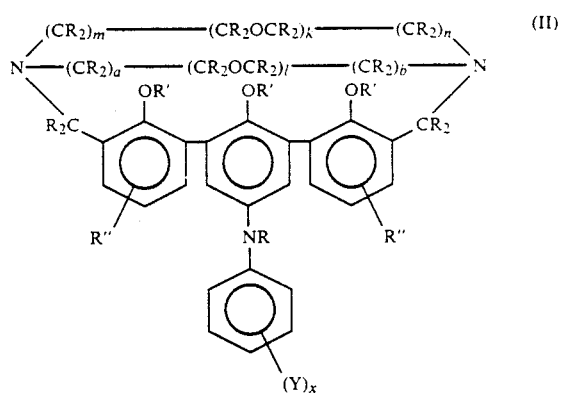

(II)

wherein:
R, same or different, is hydrogen, lower alkyl, lower alkylidene, lower alkenyl, allyl, aryl or benzyl;
R', same or different, is lower alkyl, lower alkylidene, lower alkenyl, allyl, aryl or benzyl;
R", same or different, is hydrogen, lower alkyl, lower alkylidene, lower alkenyl, allyl, aryl or benzyl;
Z is halogen;
Y is electron withdrawing group, e.g. CN, $NO_2$, $CF_3$, COOR;
m is 1 to 3;
n is 1 to 3;
a is 1 to 3;
b is 1 to 3;
k is 1 to 3;

l is 1 to 3; and x is 2 to 4.

With reference to the above formula (II), in the chromogenic cryptahemispherand used to assay sodium, the compound is a lithium complex in which k and l can be either 1 or 2, but k and l cannot both be 2. As used hereinafter, chromogenic cryptahemispherand (1.1) refers to the compound of formula (II) wherein k and l are both 1. Chromogenic cryptahemispherand (2.1) refers to the compound of formula (II) wherein k is 1 or 2, and l is 1 or 2.

As mentioned earlier, chromogenic ionophores are usually purified by chromatography and chromatographic materials such as silica gel and alumina have high sodium content. It has been found that both chromogenic cryptahemispherand (1.1) and (2.1) have a high propensity toward sodium, thus any physical contact with materials containing this ion must be avoided. Due to stringent spectral requirements, sodium contamination of chromogenic cryptahemispherands (1.1) and (2.1) higher than 0.5% by weight disqualifies the compound from use in a sodium assay. The gel chromatographic purification method of the above U.S. Pat. No. 4,859,606 was found to be adequate when producing laboratory quantities of the purified chromogenic cryptahemispherands since the percentage yield of purified material was not critical. It was found, however, that such compounds could not be isolated in commercial quantities uncontaminated since during gel chromatography they scavenged alkali metal ions from the chromatographic materials and thus became tainted or poisoned. Attempted chromatographic purification of chromogenic cryptahemispherand (1.1) and (2.1) pursuant to the teachings of the aforenoted U.S. Pat. No. 4,859,606 afforded only a small fraction of the sodium-free material while most of the product was poisoned by sodium and therefore could not be used further in a sodium assay such as that disclosed and claimed in U.S. Pat. No. 4,859,606.

In U.S. Pat. No. 4,845,212, I describe a streamlined, simplified process for the preparation of compounds of formula (II), which process also includes purification by gel chromatography. It has been found that the same problems with contamination of the final compound arose in this process as well.

Elemental analysis of different types of silica gel and alumina which are commonly used chromatographic materials revealed the presence of abundant quantities of sodium ion (e.g. silica gel from Merck & Co., Inc. was assayed at 6.42 g Na+/kg; silica gel from J. T. Baker was assayed at 6.49 g Na+/kg) which could not be removed from the chromatographic material by an easy and economical way. Besides, even if this removal were successful, chromatographic purification would be costly and impractical for large scale commercial production of the chromogenic cryptahemispherands.

It is thus desirable to develop a purification procedure for such compounds which are susceptible to deactivation by sodium ion, as well as one which is highly cost effective as opposed to gel chromatography.

I have discovered that it is possible to circumvent the problem of sodium "poisoning" of the chromogenic cryptahemispherands by applying a non-chromatographic purification procedure. The procedure exploits differences between solubilities of the reaction mixture components. Gradual removal of unreacted organic components, inorganic salts and polymeric material leads to a pure, uncontaminated product. This approach proved to be the only practical way of producing sodium-free chromogenic cryptahemispherands (1.1) and (2.1), which exhibit extraordinary propensity toward the omnipresent sodium ion.

SUMMARY OF THE INVENTION

Among the several objects of the present invention, it may be noted the development of a non-chromatographic purification process which protects certain compounds, e.g. chromogenic cryptahemispherand from being "deactivated" by sodium ion. The non-chromatographic procedure is highly cost effective as opposed to chromatography, and uses differences in solubilities of the product and undesired byproducts present in the crude reaction product.

Other objects of the invention will be in part apparent and in part pointed out hereinafter.

The invention is the process for the purification of large quantities of sodium-free chromogenic cryptahemispherands (1.1) and (2.1) of formula (II):

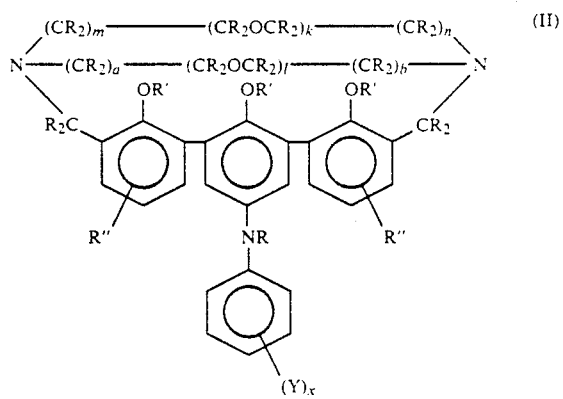

wherein:

R, same or different, is hydrogen, lower alkyl, lower alkylidene, lower alkenyl, allyl, aryl or benzyl;

R', same or different, is lower alkyl, lower alkylidene, lower alkenyl, allyl, aryl or benzyl;

R", same or different, is hydrogen, lower alkyl, lower alkylidene, lower alkenyl, allyl, aryl or benzyl;

Z is halogen;

Y is electron withdrawing group, e.g. CN, NO$_2$, CF$_3$, COOR;

m is 1 to 3;

n is 1 to 3;

a is 1 to 3;

b is 1 to 3;

k is 1 to 2;

l is 1 to 2;

k and l cannot both be 2; and x is 2 to 4.

The term "lower alkyl" as used in the present disclosure includes an alkyl moiety, substituted or unsubstituted, containing 1–4 carbon atoms. Included in the meaning of lower alkyl are methyl, ethyl, n-propyl, isopropyl, n-butyl and tert-butyl.

"Lower alkylidene" is used herein in the same context as "lower alkyl", but designates an alkylene group (i.e. a divalent alkyl) having 1–4 carbon atoms. The term lower alkylidene includes, but is not limited to, methylene, ethylidene, n-propylidene, isopropylidene, n-butylidene, sec-butylidene and tert-butylidene.

The term "aryl" as used herein includes substituted or unsubstituted aryl moieties containing 6–12 carbon atoms, such as, for example, phenyl, tolyl, butyl phenyl, naphthyl ethyl, chlorophenyl, nitrophenyl and carboxyphenyl.

"Lower alkenyl" as used herein designates a lower alkenyl moiety, substituted or unsubstituted, having 1–4 carbon atoms and includes, for example, ethenyl, 1-propenyl, 2-propenyl, isopropenyl, 1-butenyl, 2-butenyl, 3-butenyl, isobutenyl and tert-butenyl.

The term "alkyl" as used in the present disclosure includes substituted or unsubstituted moieties containing from 1 to 12 carbon atoms, and includes, for example, methyl, butyl, isobutyl and octyl.

The term "allyl" as used in the present disclosure includes substituted or unsubstituted moieties containing from 3 to 12 carbon atoms, such as, for example, 2-propene, 2-methylpropene and 2-butene.

The term "alkylidene" designates substituted or unsubstituted moieties containing from 2 to 12 carbon atoms, and includes, for example, 1,2-ethylidene, 1,2-propylidene, 3,4-hexylidene.

The above moieties may be unsubstituted or substituted as noted providing any such substituents do not interfere with the operation or functioning of the presently claimed invention.

To the extent the disclosures of the aforenoted U.S. Pat. Nos. 4,859,606 and 4,845,212 are not specifically recited herein, they are to be incorporated herein by reference. In U.S. Pat. No. 4,845,212, the final stage of the multistep synthesis of chromogenic cryptahemispherands 1 (1.1) or (2.1) of formula (II) involves cyclization between a dibromide 2 and a diazacorand 3 in the presence of lithium carbonate in acetonitrile in accordance with the following reaction:

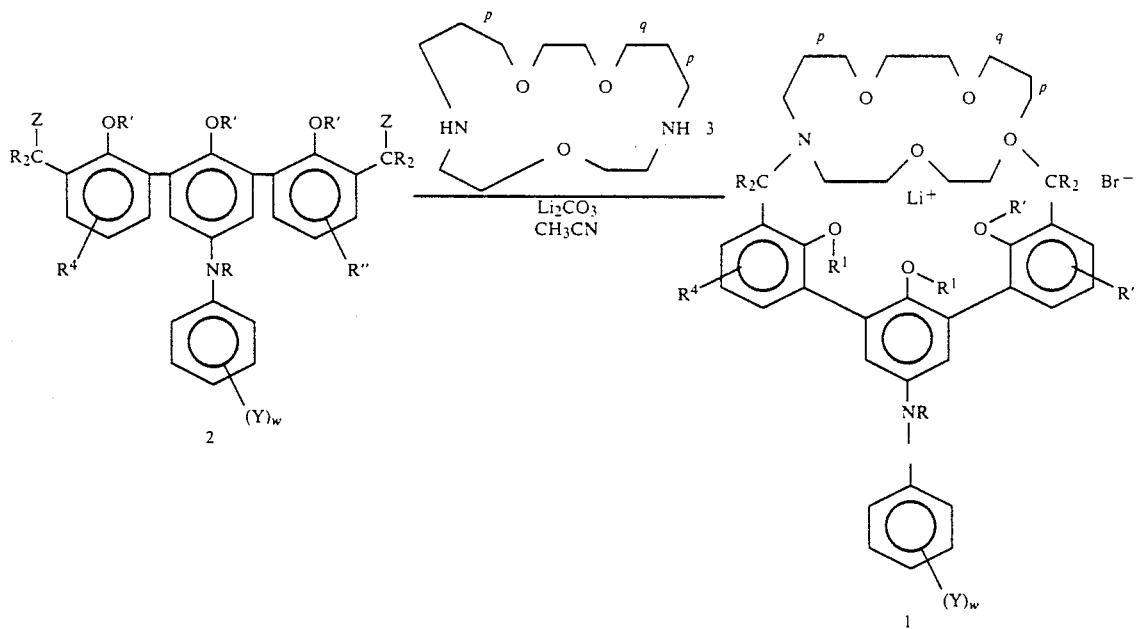

where
if $p=q=0$, diazacorand 3 is diaza-12-crown-4.
if $p=1$, $q=0$, diazacorand 3 is diaza-14-crown-4.
if $p=0$, $q=1$, diazacorand 3 is diaza-15-crown-5.

In the case of chromogenic cryptahemispherand (1.1), the cyclization reaction involves dibromide and diaza-12-crown-4, or diaza-14-crown-4. In the case of chromogenic cryptahemispherand (2.1), the reaction involves dibromide and diaza-15-crown-5.

In accordance with the present invention, the crude reaction product obtained after removal of the solvent usually contains about 60% of compound 1, the unreacted substrates (dibromide -2 and diazacorand 3), the inorganic salts (lithium carbonate and lithium bromide formed in the reaction) and polymeric material. The unreacted substrates are removed by repeated washing with ethyl acetate or other similar solvent, e.g. ethyl ether, butyl acetate, methyl acetate, 3-heptanone. The solid residue is treated with methylene chloride or other suitable chlorinated solvent, e.g. chloroform, 1,2-dichloroethane, which dissolves compound 1 and some of the lower molecular weight polymer. The inorganic material and higher molecular weight polymer are filtered. Ethyl acetate or similar solvent is then added slowly to the filtrate to precipitate the remaining impurities. This operation is monitored by thin layer chromatography (TLC). The final product obtained after the solvent is removed from the supernatant solution shows acceptable spectral characteristics and can be used in the reagent formulation.

DETAILED DESCRIPTION OF THE INVENTION

The invention is an economical and environmentally desirable process for producing large quantities of compounds of formula (II) which can be used in a colorimetric assay for sodium in aqueous solutions such as blood serum, plasma and other biological fluids.

Issued U.S. Pat. Nos. 4,859,606 and 4,845,212 disclose two syntheses for the compounds of formula (II) generally referred to as chromogenic cryptahemispherands. As the final stages in the multistep synthesis disclosed in U.S. Pat. No. 4,845,212, cyclization occurs between a dibromide 2 and a diazacorand 3. In the case of chromogenic cryptahemispherand (1.1), the cyclization reaction involves dibromide and diaza-12-crown-4 or diaza-14-crown-4. In the case of chromogenic cryptahemispherand (2.1), the reaction involves dibromide and diaza-15-crown-5.

In accordance with the invention, the crude reaction product which usually contains about 60% of the desired product compound 1, unreacted substrates, inorganic salts and polymeric materials is treated with a solvent, preferably ethyl acetate or similar solvent such as ethyl ether, butyl acetate, methyl acetate, 3-heptanone, and stirred for 30 minutes. The supernatant solution which contains unreacted substrates (dibromide and diazacorand) is than decanted and the whole operation is repeated two more times. Next, the residue is treated with a chlorinated solvent, preferably methylene chloride and stirred for 15 minutes. Other suitable solvents such as chloroform, 1,2-dichloroethane may be used. The insoluble inorganic salts and higher molecular weight polymer are filtered and a solvent which works as a precipitant for the polymeric by-products, preferably ethyl acetate or ethyl ether is added slowly with stirring. The removal of polymers is monitored by thin layer chromatography. The addition of the precipitant is terminated when the solution contains only the final product. Evaporation of the solvent provides the sodium-free cryptahemispherand.

The following working examples describe experiments which were performed in developing the present invention. Standard commercially available reagent grade chemicals were used whenever possible. These working examples are to be considered illustrative of the present invention and should not be interpreted a limiting its scope.

EXAMPLE 1

To determine the effectiveness of the gel chromatography purification method to produce sodium-free chromogenic cryptahemispherands, the following experiment was performed.

A sample (2.30 g) of the crude reaction product obtained pursuant to the synthesis described and claimed in my U.S. Pat. No. 4,845,212 was chromatographed on a column made of silica gel (100 g). The column was "preconditioned" by extensive washing with a mixture of methylene chloride-methanol (95:5, v/v) in an attempt to remove sodium from the gel. The unreacted dibromide 2 was eluted first, followed by the chromogenic product 1 (0.79 g) which was found by atomic absorption to contain about 7% sodium. Only a small isolated later fraction (80 mg) of the chromogenic product 1 had a sodium content of less than 1%. Therefore, only about 10% of the chromogenic product 1 produced was substantially free of sodium and useful in a sodium assay. The substantially free sodium compound represented approximately 3% of the crude reaction product.

EXAMPLE 2

To demonstrate the effectiveness of the present invention, the following example was performed.

A batch of the crude reaction product (37 g) is suspended in ethyl acetate (500 ml) and stirred vigorously for 0.5 hours to dissolve unreacted organic substrates. The red colored supernatant solution is decanted and the whole operation is repeated two more times. The solid residue is then treated with methylene chloride (500 ml), stirred for 15 minutes and the insoluble material is filtered through a funnel with fritted glass. Ethyl acetate (about 1 liter total) is added dropwise with stirring to the filtrate. The removal of the polymeric material is followed by thin-layer chromatography using silica gel and a mixture of methylene chloride and methanol (85:15, v/v) as eluent. The addition of ethyl acetate is terminated when only the desired product, i.e. purified compound 1, is present in the solution. The solvent is removed in vacuo to produce 15 g of chromogenic compound 1 with acceptable spectral characteristics. In an ethoxyethoxyethanol solution at pH 7.30, the peak wavelength maximum should appear in a 370–380 nm region.

In contrast to the yield from the gel purification as exemplified in Example 1, the substantially sodium-free compound represented approximately 40% of the crude reaction product.

The above examples demonstrate the superiority of the non-chromatographic purification method over that of the gel purification.

Some of the advantages of the present invention evident from the foregoing description include a non-chromatographic purification of compounds, e.g. chromogenic cryptahemispherands, which are susceptible to deactivation by sodium ion. The procedure is highly cost effective as opposed to chromatography, and uses differences in solubilities of the product and undesired by-products present in the crude reaction mixture.

In view of the above, it will be seen that the several objects of the inventions are achieved and other advantageous results attained.

It should be understood by those skilled in the art that various modifications may be made in the present invention without departing from the spirit and scope thereof as described in the specification and defined in the amended claims.

What is claimed is:

1. A method for the non-chromatographic purification of chromogenic cryptahemispherands of the following formula (II):

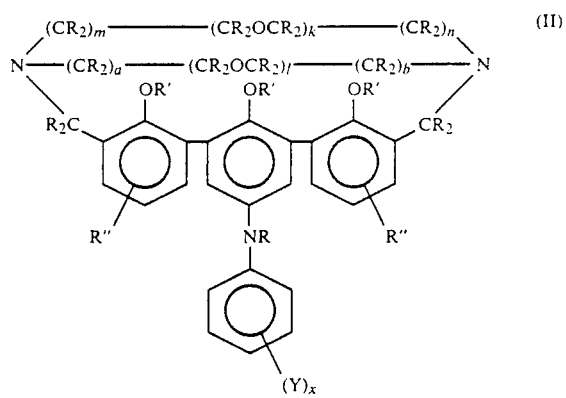

wherein:
R, same or different, is hydrogen, lower alkyl, lower alkylidene, lower alkenyl, allyl, aryl or benzyl;
R', same or different, is lower alkyl, lower alkylidene, lower alkenyl, allyl, aryl or benzyl;
R'', same or different, is hydrogen, lower alkyl, lower alkylidene, lower alkenyl, allyl, aryl or benzyl;
Z is halogen;
Y is electron withdrawing group;
m is 1 to 3;
n is 1 to 3;
a is 1 to 3;
b is 1 to 3;

k is 1 to 2;
l is 1 to 2;
k and l are not both 2; and
x is 2 to 4, from a reaction mixture which includes unpurified compound of formula (II), unreacted organic components, inorganic salts and polymeric material, which method comprises the steps of:

(a) removing said unreacted substrates by repeated washing of said reaction mixture with a first solvent to obtain a solid residue;

(b) treating said solid residue with a chlorinated solvent to dissolve the compound of formula (II) and lower molecular weight polymers and form a supernatant;

(c) filtering said inorganic material and higher molecular weight material from said supernatant to form a filtrate;

(d) treating said filtrate of step (c) with a second solvent to precipitate the remaining polymeric material from said filtrate; and (e) removing said second solvent from said filtrate to obtain the compound of formula (II) free of sodium.

2. The method of claim 1 wherein said unreacted substrates include dibromide and diazacorands.

3. The method of claim 1 wherein said inorganic salts include lithium carbonate and lithium bromide.

4. The method of claim 1, wherein in formula (II), k and l are both 1, and said unreacted organic components include dibromide and diaza-12-crown-4 or diaza-14-crown-4.

5. The method of claim 1 wherein formula (II), k is 1 or 2, and l is 1 or 2, and said unreacted organic components include dibromide and diaza-15-crown-5.

6. The method of claim 1 wherein said first solvent is selected from the group consisting of ethyl acetate, ethyl ether, butyl acetate, methyl acetate and 3-heptone.

7. The method of claim 1 wherein said chlorinated solvent is selected from the group consisting of methylene chloride, chloroform and 1,2-dichloroethane.

8. The method of claim 1 wherein said second solvent is ethyl acetate.

* * * * *

UNITED STATES PATENT AND TRADEMARK OFFICE
CERTIFICATE OF CORRECTION

Page 1 of 2

PATENT NO. : 5,064,955
DATED : November 12, 1991
INVENTOR(S) : Bronislaw P. Czech It is certified that error appears in the above-identified patent and that said Letters Patent is hereby corrected as shown below:

Column 2, formula (1) should read as follows:

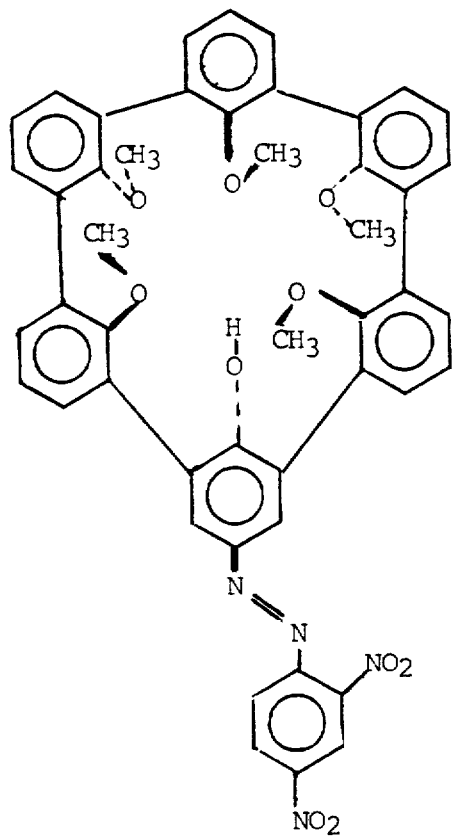

UNITED STATES PATENT AND TRADEMARK OFFICE
CERTIFICATE OF CORRECTION

PATENT NO. : 5,064,955

DATED : November 12, 1991

INVENTOR(S) : Bronislaw P. Czech

Page 2 of 2

It is certified that error appears in the above-indentified patent and that said Letters Patent is hereby corrected as shown below:

Columns 5 and 6, lines 36 through 59, the formula should read as follows:

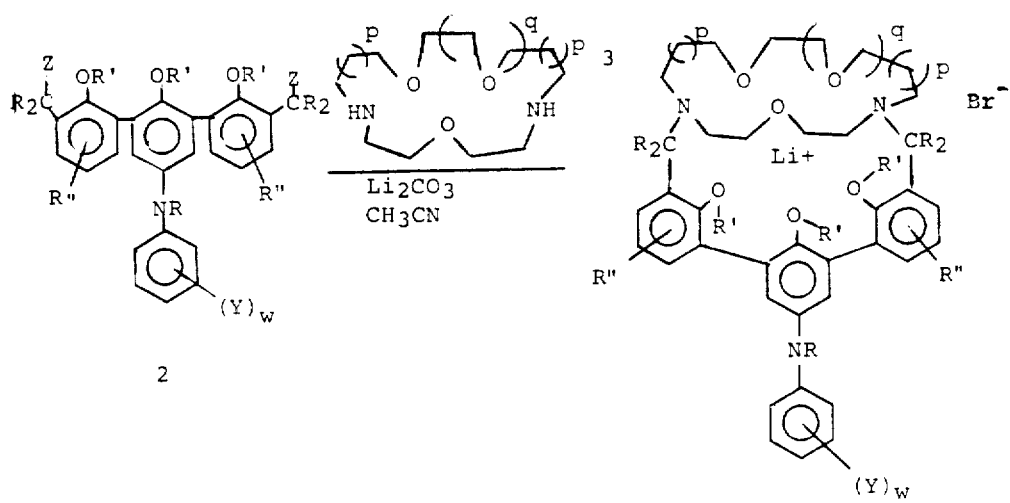

Signed and Sealed this

Twenty-eighth Day of September, 1993

Attest:

BRUCE LEHMAN

Attesting Officer

Commissioner of Patents and Trademarks